United States Patent [19]

Barnavon et al.

[11] Patent Number: 4,897,427
[45] Date of Patent: Jan. 30, 1990

[54] METHOD OF COMBATTING PRUNING WOUND DISEASES

[75] Inventors: Marc Barnavon, La-Seine-St.-Cloud; Philippe Dutruel, Rueil-Malmaison; René Ravaux, Lardy, all of France

[73] Assignee: Sandoz Ltd., Basel, Switzerland

[21] Appl. No.: 144,887

[22] Filed: Jan. 14, 1988

[30] Foreign Application Priority Data

Jan. 14, 1987 [FR] France ................... 8700309
Jan. 14, 1987 [FR] France ................... 8700311

[51] Int. Cl.⁴ .................. A61K 9/12; A61K 3/41; A61K 31/395
[52] U.S. Cl. .................. 514/383; 424/47; 424/195.1; 514/384; 514/385; 514/396; 514/403
[58] Field of Search ........................ 514/383

[56] References Cited

U.S. PATENT DOCUMENTS

| | | | |
|---|---|---|---|
| 3,773,926 | 11/1973 | Knowles et al. | 424/78 |
| 4,472,415 | 9/1984 | Worthington et al. | 514/383 |
| 4,551,469 | 11/1985 | Parry et al. | 514/383 |
| 4,623,654 | 11/1986 | Parry et al. | 514/383 |
| 4,654,332 | 3/1987 | Parry et al. | 514/383 |

FOREIGN PATENT DOCUMENTS

| | | | |
|---|---|---|---|
| 0047594 | 3/1982 | European Pat. Off. | 424/78 |
| 1573941 | 6/1969 | France | 424/78 |
| 2584261 | 1/1987 | France | 424/78 |
| 8700001 | 1/1987 | PCT Int'l Appl. | 424/78 |
| 677086 | 8/1952 | United Kingdom | 424/78 |
| 2064520 | 6/1981 | United Kingdom | 424/78 |
| 2136423 | 9/1984 | United Kingdom | 424/78 |

OTHER PUBLICATIONS

Chemical Abstracts 105:42818q (1986).
Chemical Abst. 99:100835p (1983).
Chem. Abst. 89:85653a (1978).

Gendle, et al. 1981 "Preparation for Treatment of Pruning Wounds" Pestic. Sci. v12: 313–318.
Chem. Abstr. v106(19) 1987 Abstr. Nos. 151482s and 151483t.
Chem. Abstr. v99 1983 Abstr. No. 100630h.
Matthee 1982 "Die Behandling von Schnittwunden an Obstbaümen und Weinreben mit ®Baycor und ®Bayleton" Pflanzen.–Nach. Bayer v35: 134–151.
Chem. Abstr. v100 (1984) Abstr. No. 46865x.
Mercer et al. 1983 "Chemical treatments for Control of Decay in Pruning Wounds" Ann. Appl. Biol. v102: 435–53.
Bolay 1986 "Comment proteger la vigne et les arbres fruitiers des attaques d'entypiose?" Rev. Suisse Vitic. Arboric. Hortic. 18(1) 7–13.

Primary Examiner—Dale R. Ore
Attorney, Agent, or Firm—Gerald D. Sharkin; Richard E. Vila; Joanne M. Giesser

[57] ABSTRACT

The invention relates to a method of combatting pruning wound diseases in plants employing a compound of the formula

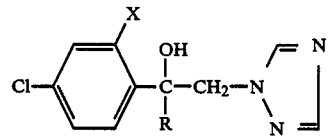

wherein X is H or Cl and R is butyl, 1-cyclopropylethyl or 1-cyclopropyl-1-methylethyl, or associations of a compound of the formula with appropriate fungicides.

The invention comprises also hydrophobic compositions for combatting pruning wound diseases, comprising an effective amount of an appropriate fungicide and/or bactericide in an oily, thixotropic, hydrophobic non-phytotoxic medium.

16 Claims, No Drawings

METHOD OF COMBATTING PRUNING WOUND DISEASES

The present invention relates to a method of combatting pruning wound diseases and to formulations suitable for such use.

Pruning wound diseases are diseases in ligneous plants caused by fungi or bacteria parasiting pruning wounds of plants, which can lead to loss or damage of such plants. One very important pruning wound is caused by Eutypa armenicae, a fungus of the family of the Ascomycetes, also known under the name Eutypa lata (see B. Dubos et al., Phytoma, Défense des cultures, July-August 1980, pages 13-15 and A. Bolay, Revue Suisse de Vitic. Arboric, Hortic 16, 265-273 (1984). The disease caused by E. lata is generally referred to as "eutypiosis".

Various compounds such as benodanil, bitertanol, triadimenol, triadimefon, captafol, pyracarbolid and in particular benzimidazol derivatives such as carbendazim have been proposed and/or used for combatting pruning wound diseases. These compounds could however not avoid a dramatic territorial expansion of such diseases.

It has now been found that the compounds of the formula

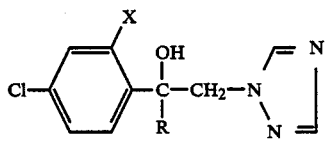

wherein X is H or Cl
and R is butyl, 1-cyclopropylethyl or 1-cyclopropyl-1-methyl-ethyl are particularly appropriate for combatting pruning wound diseases.

Where R is butyl, it is preferably n-butyl or tert.-butyl.

Preferred compounds of formula I are the compound in which X is Cl and R is n-butyl, the compound in which X is H and R is 1-cyclopropyl-ethyl and the compound in which X is H and R is 1-cyclopropyl-1-methylethyl.

The compounds of formula I are conveniently employed in free form or in agriculturally acceptable acid addition salt form.

The compounds of the formula are known fungicides. They have not however been suggested for use for combatting pruning wound diseases such as eutypiosis.

The compounds of the formula and in particular 2-(4-chlorophenyl)-3-cyclopropyl-1-(1H-1,2,4-triazole-1-yl)-butane-2-ol, have a remarkable fungicidal activity against fungi and bacteria responsible for pruning diseases of perennial plants.

They are in particular effective against *Cylindrocarpon mali* on fruit trees, *Cytospora cincta* on peach trees, *Erwinia amylovora* on fruit trees, *Pseudomonas syringae* and spp. on fruit trees, *Agrobacterium tumefaciens* on vines, *Erwinia vitivora* on vines, *Stereum hirsutum* on vines and *Eutypa lata* on fruit trees and vines.

The compounds of the formula may be used for combatting pruning wound diseases, in particular eutypiosis on perennial plants which are pruned during their period of vegetative rest to increase the number of fruit or flower buds and/or to improve their quality.

The invention accordingly provides a method of combatting pruning wound diseases in plants, which comprises applying to the pruning wounds a fungicidally and bacterially effective amount of a compound of the formula.

Examples of perennial plants which may be treated according to the method of the invention are fruit crops including apricot, mango, prune, peach, apple, pear, cherry, quince, black current, red and white current, walnut, fig, kaki, elder and citrus plants, rose cultures, perennial horticultural plants and ornamentals, and particularly grape vine.

The compounds of the formula may and preferably are applied in association with further fungicides, e.g. with contact fungicides such as folpet, thiram, and copper fungicides and in particular with benzimidazole fungicides such as benomyl and carbendazime, preferably with the latter.

Appropriate bactericides may be added as well. Examples of bactericides which may be employed in conjunction with the compounds of formula are organic bactericides such as blasticidine, cycloheximide, griseofulvine, kanigamycine, oxytetracyclin, streptomycin, validamycine, oxine-copper, nitrapyrin, dithianon Na-pyrion, calvinphos, fluméquine and bactericidal quaternary ammonium salts such as cetyltrimethylammonium chloride.

In the method of the invention the compounds of the formula, either alone or in association with other fungicides and/or bactericides, are conveniently employed in fungicidal composition form.

Such compositions may be produced in conventional manner, e.g. by mixing a compound of the formula and eventually other active ingredients with appropriate adjuvants such as diluents and optionally other formulating ingredient such as surfactants, pigments, thickeners and the like.

The application of such compositions to the pruning wounds should be effected with the utmost care such that essentially all pruning wounds are treated. The composition should preferably also have a satisfactory stickerability so as not to be rinsed off by the rain and also to provide protection against infections.

Spray and dust applications may accordingly not give the desired results. A more convenient and effective mode of application is with the aid of pruning shears fitted with a container from which a formulation comprising the active ingredient will be applied onto and distributed over an appropriate area of one or both blades, e.g. the cutting blade while pruning. Various pruning shears fitted with such container system have been described in the literature (i.a. in the French Patent Application 85.10206). However, the formulations hitherto suggested for application by such pruning shears do all have certain disadvantages such as, inappropriate viscosity, unsatisfactory stickerability etc.

The invention now provides formulations which are particularly appropriate for application by pruning shears.

Such formulations comprise
(a) a pruning wound disease combatting effective amount of active ingredient (eg. a fungicide and/or a bactericide suitable for treatment of pruning wound disease) and
(b) an oily, thixotropic, hydrophobic, non-phytotoxic medium, the formulation being exempt from water.

The term thixotropic refers to a medium which is viscous when at rest and liquid when moved, e.g. by agitation or compression.

The oily, thixotropic, hydrophobic, non-phytotoxic medium consists essentially of a non-phytotoxic, hydrophobic oil and a non-phytotoxic, thixotropic adjuvant.

The non-phytotoxic, hydrophobic oil may e.g. be a mineral oil, a vegetable oil, an animal oil, a synthetic oil or mixtures thereof.

Suitable examples of mineral oils are vaseline and paraffine oil. Suitable examples of vegetable oils are peanut oil, croton oil, coffee oil, castor oil, almond oil, walnut oil, palm oil, coconut oil, flax oil, poppy seed oil, olive oil, grape seed oil, sesame oil, hemp seed oil, corn germ oil, sunflower oil, soybean oil, rape oil, cotton seed oil and mixtures thereof.

Suitable example of animal oils are fish oils, seal oil, whale oil, cod liver oil, and ox trotter oil.

Suitable examples of synthetic oils are hydrogenated oils or mixtures thereof with epoxydated vegetable oils and mixtures of epoxydated vegetable oils. Further examples of suitable hydrophobic oils include siccative oils and silicone oils.

Preferably a mineral oil, in particular paraffine oil, or an optionally epoxydated vegetable oil or a mixture of such optionally epoxidated vegetable oil is employed. Where the hydrophobic oil is a vegetable oil or derived therefrom, such vegetable oil is preferably selected from sunflower oi and corn (maize) germ oil.

The thixotropic adjuvant is advantageously a thickener forming with the hydrophobic, oily component a thixotropic, oily hydrophobic non-phytotoxic medium. The thickener may be of natural, artificial, semi-synthetic or synthetic origin.

Examples of suitable natural thickeners comprise magnesium hydroxide, bentonite clay and colloidal silica.

Examples of suitable thickeners of animal origin are egg albumine, blood albumine, casein, bone glue or parchment glue.

Examples of suitable thickeners of vegetable origin are amylaceous materials such as maize starch, and vegetable gums, such as arabic gum, xanthan gum, tragacanth gum, carob flour gum and the gum obtained from Cyamopsis tetragonolaba. Examples of suitable artificial or semi-synthetic thickeners are modified starch products such as acid modified starches, oxydized starches, slightly reticulated starches obtained by reaction with ethylene oxide, etherified starches, carboxymethylated starches, methylated starches and hydroxyethylated starches, degradation products of starch, modified vegetable gums, alginates, carraghenates, etherified celluloses such as methyl celluloses, carbomethyl celluloses, methylhydroxyethyl celluloses, hydroxyethyl celluloses and hydroxypropylmethyl celluloses.

Examples of suitable synthetic thickners are polymeric products, for example polyvinylic alcohols and polyacrylic acids.

Particularly suitable for use in the invention are mineral thickeners, more particularly colloidal silica, in particular pyrogenated colloidal silica.

The weight ratio between the thixotropic adjuvant and the hydrophobic oil is conveniently between 0.1:99.9 and 1:9, preferably between 0.5:99.5 and 1:15, more preferably between 1:99 and 1:40 (i.e. between 1:100 and 2.5:100).

The active ingredients suitable for use in such thixotropic composition may be any fungicide or bactericide effective against pruning wounds or mixtures thereof.

Examples of fungicides suitable for use as active ingredients in the compositions of the invention are sulphur, benzimidazole derivatives such as benomyl, carbendazime and thiabendazole, or thiophanates such as ethyl thiophanate and methyl thiophanate dithiocarbamate derivatives such as thirame and mancozeb, phthalimide derivatives such as captan, folpet and captafol, ergosterol biosynthesis inhibitors, e.g. such belonging to the general class of the pyrimidines such as fenarimol, triarimol and nuarimol, such belonging to the class of the morpholines such as dodemorph, tridemorph and fenpropimorph, such belonging to the class of the imidazoles such as prochloraz, vinconazole, triflumizole and imazalil, such belonging to the class of the pyridines such as pyrifenox and buthiobate, such belonging to the class of the triazoles such as hexaconazole, flusilazole, etaconazole, triadimefon, triadimenol, propiconazole, dichlorobutrazol, bitertanol, penconazole, flutriafol and 2-(4-chlorophenyl)-3-cyclopropyl-1-(1H-1,2,4-triazole-1-yl)-butane-2-ol, copper fungicides including copper-(II)carbonate, copper(II)calcium sulphate, copper(II)-calcium oxychloride, tetracupric oxychloride, burgundy mixture, bordeaux mixture, cuprous oxide, cupric hydroxide, copper(II)oxychloride and copper complexes such as $[Cu-N(CH_2CH_2OH)_3](OH)_2$, $[Cu(NH_2CH_2CH_2NH_2)_2]SO_4$ and mixtures of such fungicides.

Examples of bactericides suitable for use as active ingredients in the compositions of the invention are those bactericides, enumerated hereinabove as suitable for use in conjunction with the compounds of the formula in the method of the invention.

Preferred compositions of the invention comprise as active ingredient copper fungicides such as copper oxychloride and copper sulphate (e.g. of the tetracupric tricalcium type), benomyl, carbendazime, thirame, folpet, ergosterol biosynthesis inhibitors, in particular those belonging to the class of the triazoles, more preferably the compounds of the formula, most preferably hexaconazole or 2-(4-chlorophenyl)-3-cyclopropyl-1-(1H-1,2,4-triazole-1-yl)-butane-2-ol) (especially the latter), and mixtures thereof.

Preferred fungicide mixtures include compositions comprising carbendazim, thirame, folpet and optionally a copper fungicide and/or a bactericide such as cetyltrimethylammonium chloride and compositions comprising hexaconazole or more preferably 2-(4-chlorophenyl)-3-cyclopropyl-1-(1H-1,2,4-triazole-1-yl)-butane-2-ol and optionally carbendazim.

The hydrophobic formulations of the invention comprise conveniently from 0.5 to 10% by weight, more preferably from 1 to 5% by weight of active ingredient(s).

These hydrophobic formulations of the invention may also comprise further adjuvants, e.g. dyestuffs to control the distribution of the composition on the pruning wounds, surfactants to secure spreading of the formulation over the pruning wound surface, co-solvents, anti-freezing agents, antioxydants etc.

The hydrophobic formulation of the invention have conveniently a viscosity of from 200 to 1500, preferably from 500 to 1200 cp and more preferably from 800 to 1000 cp. Such viscosity is determined using a Brookfield Visosimeter Model RVF-100 and Spindle No. 2 at a speed of 20 RPM. They are applied as a thin layer covering the total surface of the pruning wound.

The hydrophobic formulations of the invention form, immediately after their application, a hydrophobic layer protecting the active ingredient(s) comprised in the formulation against washing out. Moreover, the formulations comprising a vegetable oil as hydrophobic oil have the advantage that they facilitate penetration of the active ingredient(s).

The invention is illustrated by the following examples, wherein parts and percentages are by weight.

EXAMPLE 1

10 Parts of a compound of the formula (e.g. 2-(4-chlorophenyl)-3-cyclopropyl-1-(1H-1,2,4-triazole-1-yl)butane-2-ol) are mixed with 4 parts of fine, synthetic silica, 3 parts of sodium lauryl sulphate, 7 parts of sodium lignin sulphonate, 66 parts of finely divided kaolin and 10 parts of diatomaceous earth, and the mixture is ground until reaching an average particle size of about 5 microns. A wettable powder is obtained, which can be diluted in water before being used in the form of a spray liquor which can be applied by spraying.

EXAMPLE 2

10 Parts of a compound of the formula are mixed with 10 parts of an emulsifier and 80 parts of isopropanol. The emulsifiable concentrate is diluted with water to the desired concentration.

EXAMPLE 3

One part of the compound of the formula (e.g. 2-(4-chlorophenyl)-3-cyclopropyl-1-(1H-1,2,4-triazole-1-yl)butane-2-ol) is ground until the particle size is in the order of one micron. 97 parts of sunflower oil are added whilst stirring vigorously, followed by 2 parts of pyrogenic colloidal silica, and stirring continues until a homogeneous mixture is obtained. A fine, hydrophobic, thixotropic dispersion is thus obtained.

EXAMPLE 4

The process is as described in Example 3, but the sunflower oil is replaced with paraffin oil or corn germ oil.

EXAMPLE 5

The process is as described in Example 3, but the compound of the formula is replaced with carbendazim.

EXAMPLE 6

The process is as described in Example 5, but the sunflower oil is replaced with paraffin oil.

EXAMPLE 7

The process is as described in Example 5, but corn oil is used instead of the sunflower oil

EXAMPLE 8

The process is as described in any one of Examples 5 to 7, but using one part of folpet instead of carbendazim.

EXAMPLE 9

The process is as described in any one of Examples 5 to 7, but using one part of benomyl instead of carbendazim.

EXAMPLE 10

The process is as described in any one of Examples 5 to 7, but using one part of methyl thiophanate instead of carbendazim.

EXAMPLE 11

The process is as described in any one of Examples 5 to 7, but using one part of thiram instead of carbendazim.

EXAMPLE 12

The process is as described in any one of Examples 5 to 7, but using one part of hexaconazole instead of carbendazim.

EXAMPLE 13

The process is as described in any one of Examples 5 to 7, but using one part of a 30:230:430 mixture of carbendazim:thiram:folpet or of a 75:500 mixture of carbendazim:folpet or of a 75:375 mixture of carbendazim:captan instead of carbendazim.

EXAMPLE 14

The process is as described by any one of Examples 5 to 7, but using 1 part of a 1.25:1 mixture of carbendazim: 2-(4-chlorophenyl)-3-cyclo-propyl-1-(1H-1,2,4-triazol-1-yl)-butan-2-ol.

EXAMPLE 15

One part of carbendazim comprising 100% active material is ground with 4 parts of tetracupric tricalcium copper sulphate comprising 27% active material, until the size of the particles is in the order of 1 micron. Then, 93.8 parts of paraffin oil and 1.2 parts of pyrogenic colloidal silica are added whilst stirring vigorously, and stirring continues until a homogeneous mixture is obtained. A fine, hydrophobic, thixotropic dispersion is thus obtained with a viscosity of 900 cp.

EXAMPLE 16

The process is as described in Example 15, but the paraffin oil is replaced with sunflower oil or corn germ oil.

EXAMPLE 17

The process is as described in Example 15 or 16, but the carbendazim is replaced with one part of folpet, benomyl or of a 230:30:430 mixture of thiram:carbendazim:folpet.

EXAMPLE 18

One part of carbendazim comprising 100% active material and 2 parts of copper oxychloride comprising 57% active material are ground until the size of the particles is in the order of one micron. Then, 95 parts of paraffin oil, followed by 2 parts of pyrogenic, colloidal silica are added whilst stirring vigorously, and stirring continues until a homogeneous, hydrophobic, thixotropic mixture is obtained.

EXAMPLE 19

The process is as described in Example 18, but sunflower oil or corn germ oil is used instead of the paraffin oil.

EXAMPLE 20

The process is as described in Example 18 or 19, but instead of carbendazim, folpet, benomyl or a 230:30:430 mixture of thiram:carbendazim:folpet is used.

EXAMPLE 21

One part of carbendazim comprising 100% active material, 2 parts of copper oxychloride comprising 57% active material and 0.5 parts of cetyl trimethylammonium chloride are ground until the size of the particles in the order of one micron. Then 95.3 parts of paraffin oil are added whilst stirring vigorously, followed by 1.2 parts of pyrogenic, colloidal silica, and stirring continues. A homogeneous, hydrophobic, thixotropic mixture is thus obtained.

EXAMPLE 22

The process is as described in Example 21, but the paraffin oil is replaced with sunflower oil or corn germ oil.

EXAMPLE 23

The process is as described in Example 21 or 22, but the carbendazim is replaced with one part of folpet, benomyl or a 30:230:430 mixture of carbendazim:thiram:folpet.

EXAMPLE 24

The vine is pruned using a cutting device and using simultaneous treatment for the stem of a plant, such as that described in French Patent Application 85 10206 or International Patent Application WO 86 00229. The device is provided with a valve containing the formulation described in Example 3 or 4. Whist cutting the stem, the device allows the formulation to be applied to the pruning wound. The formulation does not leach and remains intact on the wound for a long period in spite of adverse weather conditions. In this way, the wound is well protected against Eutypa lata.

EXAMPLE 25

In Example 24, the formulation of example 3 or 4 is replaced with any one of the formulations described in Examples 5 to 23. Similarly good results are obtained.

We claim:

1. The method of combatting pruning wound diseases caused by microorganism selected from the group consisting of *Cylindrocarpon mali, Cytospora cincta, Erwinia amylovora, Pseudomonas spp., Agrobacterium tumefaciens, Erwinia vitivora, Stereum hirsutum* and *Eutypa lata* in pruning wounds on trees and perennial vines subject to infection by such microorganism, comprising applying to the pruning wound on a tree or perrenial vine subject to infection by such a micoorganism a composition comprising a pruning wound disease combatting effective amount of a compound of the formula

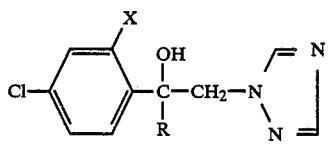

wherein

X is H or Cl, and

R is butyl, 1-cyclopropyl-ethyl or 1-cyclopropyl-1-methyl-ethyl, said compound being in free base form or in agriculturally acceptable acid addition salt form.

2. The method of claim 1 in which entypiosis caused by *Eutypa lata* is combatted.

3. The method of claim 1 in which X is Cl and R is n-butyl.

4. The method of claim 1 in which X is H and R is 1-cyclopropyl-ethyl.

5. The method of claim 1, in which the active ingredient additionally comprises carbendazime.

6. In a method of combatting pruning wound diseases in perennial plants comprising pruning the plants with pruning shears fitted with a container from which a composition comprising an active ingredient biologically effective to combat pruning wound disease is applied and distributed onto one or both blades of the pruning shears and then onto the resulting pruning wound, the improvement of employing therein as the composition a composition as defined in claim 1.

7. The method of claim 6 in which the active ingredient comprises a pruning would disease effective amount of 2-(4-chlorophenyl)-3-cyclopropyl-1-(1H-1,2,4-triazole-1-yl)-butane-2-ol.

8. The method of claim 1 wherein the composition comprises:
(a) from about 0.5% to 10% by weight of the compound of the formula of claim 1,
(b) a non-phytotoxic, hydrophobic oil selected from the group consisting of a mineral oil, a vegetable oil, an animal oil, a hydrogenated vegetable oil, an epoxydated vegetable oil, a siccative oil, a silicone oil and mixtures thereof, and
(c) a non-phytotoxic thixotropic thickening adjuvant forming with said hydrophobic oil a thixotropic, non-phytotoxic medium, the weight ratio of said hydrophobic oil to said thixotropic adjuvant being in the range of from 0.1:99.9 to 1:9, said composition having a viscosity of between 200 to 1500 cps as measured with a Spindle No. 2 at 20 rpm on a Brookfield Viscometer Model RVF-100, and being exempt from water.

9. The method of claim 1, wherein the non-phytotoxic, hydrophobic oil is a mineral oil, a vegetable oil, a mixture of vegetable oils, an animal oil or a hydrogenated or expoxydated vegetable oil.

10. The method of claim 9, wherein the non-phytotoxic, hydrophobic oil is a paraffin oil, sunflower oil or corn germ oil.

11. The method of claim 9, wherein the thickener is colloidal silica.

12. The method of claim 8, wherein the weight ratio thixotropic adjuvant:hydrophobic oil is between 0.5:99.5 and 1:15.

13. The method of claim 11, wherein the weight ratio thixotropic adjuvant:hydrophobic oil is between 1:99 and 1:40.

14. The method of claim 1, having a viscosity of from 500 to 1200 cp.

15. The method of claim 14, having a viscosity of from 800 to 1000 cp.

16. The method of claim 1 comprising from 1 to 5% by weight of active ingredient.

* * * * *